United States Patent [19]

Schulze

[11] 4,221,485

[45] Sep. 9, 1980

[54] OPTICAL SMOKE DETECTOR

[75] Inventor: Richard G. Schulze, Hopkins, Minn.

[73] Assignee: Honeywell Inc., Minneapolis, Minn.

[21] Appl. No.: 45,025

[22] Filed: Jun. 4, 1979

[51] Int. Cl.³ .......................................... G01N 21/01
[52] U.S. Cl. .................................. 356/338; 250/574;
340/630; 350/296
[58] Field of Search ............... 356/338, 340; 250/353,
250/574; 340/628, 630; 350/296

[56] References Cited

U.S. PATENT DOCUMENTS

| 3,226,703 | 12/1965 | Finkle .................................. 340/594 |
| 4,072,421 | 2/1978 | Coyne et al. ........................ 356/338 |

*Primary Examiner*—John K. Corbin
*Assistant Examiner*—Bruce Y. Arnold
*Attorney, Agent, or Firm*—Omund R. Dahle

[57] ABSTRACT

An optical smoke detector having a smoke sensing chamber comprising a point source of light mounted on the middle of a photodetector, the source of light transmitting in a forward direction and away from the photodetector and further having the point source of light located at the center of curvature of a spherical reflector. During normal standby periods when there are no smoke particles in the chamber to scatter the light, the light is transmitted to the spherical reflector and reflected back to the source without falling on the photodetector. In the presence of smoke the light is scattered and falls on the photodetector to indicate the presence of the smoke.

7 Claims, 4 Drawing Figures

D>λ CASE

D<λ CASE

⊚ SCATTERING EVENTS

OPTICAL SMOKE DETECTOR

BACKGROUND AND SUMMARY OF THE INVENTION

This invention relates generally to apparatus used in conjunction with fire detection and alarm systems. More particularly it relates to the field of optical smoke detectors designed to detect an annunciate the presence of smoke in the air in or moving through the device. To increase the sensitivity of the device the components of this device are arranged so that light is efficiently collected by means of a spherical reflector.

Typical photoelectric smoke detector configurations collect only a small fraction of the smoke-scattered light. This invention collects all of the light scattered through small angles in both the forward scatter and backward scatter by means of a spherical reflector. Small angle forward and backward scattering are the predominant scattering modes for particles in the size range of interest for smoke detection.

DESCRIPTION

Figure 1:
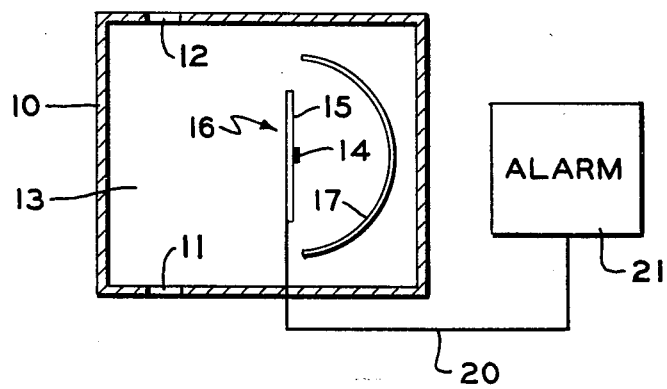
FIG. 1 of the drawings is a diagrammatic representation of the improved smoke detecting chamber.

Referring now to the drawings there is illustrated in FIG. 1 a cross section view of the smoke detector chamber. An exterior casing 10 has openings 11 and 12 in its lower and upper portions respectively for allowing air to flow through the sensing chamber 13. A souce of radiant energy such as an LED (light emitting diode) 14 is mounted on a disc shaped or rectangular shaped photodetector 15. The source of radiant energy may be, as preferred, in the visible, IR or UV spectrum, and is hereafter called light. The LED is constructed to emit light into a forward direction and does not direct illumination back on the photodetector 15. The source and detector assembly 16 are all mounted within the casing 10. In one embodiment the large area detector 15 is a photodiode model CLD31, by Clairex Corporation of New York, N.Y. This photodiode is designated to operate in the photovoltaic mode and has an active area of about 22 mm². Its peak sensitivity is in the wavelength of 0.9–1.0 microns and is well suited for use with an infrared LED as the souce 14. In this embodiment a gallium arsenide LED may be used, for example.

Figure 3:
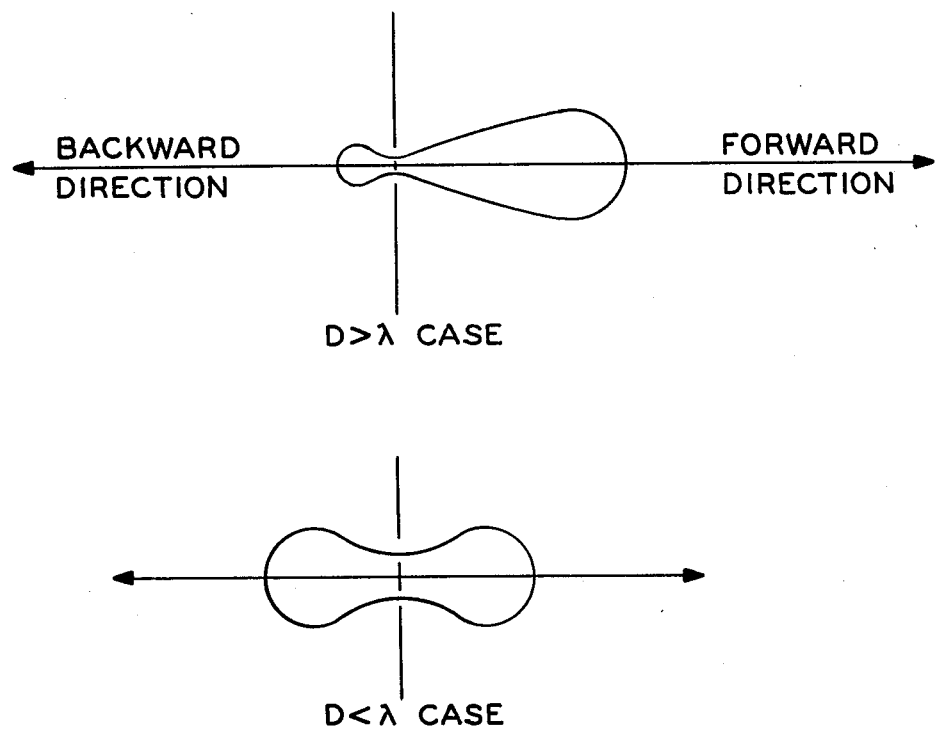
FIG. 3 is a graphical representation of forward and backward light scatter in a smoke detector vs. smoke particle size.

A spherical reflector or mirror 17 is also mounted within the smoke chamber such that the LED is at the center of curvature of the spherical surface. The small dimensions of the LED make it approximately a point source with respect to the dimensions of the reflector. Light emitted from the LED travels along a radius of the reflector 17. In the absence of smoke there is no light scatter and thus all of the light reaches mirror 17 and is reflected back to the LED and not onto the surrounding photodetector. When smoke is present the smoke particles cause a predominant forward or backward scatter of the transmitted light. The graphs of FIG. 3 show the scattered radiation pattern which exists due both to large ($D > \lambda$) and small ($D < \lambda$) smoke particles; and that for large smoke particles, e.g. the diameter D of the smoke particles is larger than the wavelength $\lambda$ of the light from souce 14, the light scatter from the particles is predominantly forward scatter with very little backward scatter, and also that for small smoke particles, e.g. the diameter of smoke particles smaller than $\lambda$, the back scatter increases and is substantially equal to the forward scatter. If a small angle forward or backward scattering event occurs, the light will not return to the LED but will impinge on the surrounding photodetector, generating a photo signal which indicates the presence of smoke particles. FIG. 1 shows the photodetector 15 being connected by a suitable electrical connection 20 to an alarm circuit 21. Detector 15, in response to light reflected from the smoke suspended within the chamber 13, causes an electrical current to flow to the alarm circuit. The alarm circuit may be an amplifier-relay combination, which when the signal from the detector reaches a predetermined magnitude, closes a circuit to activate an alarm device. Light which is not scattered will be returned to the LED where it is either reflected or absorbed, but does not generate a photo signal. To the extent that unscattered light would be reflected from the LED an effective increased path length for scattering would be realized.

Figure 2:
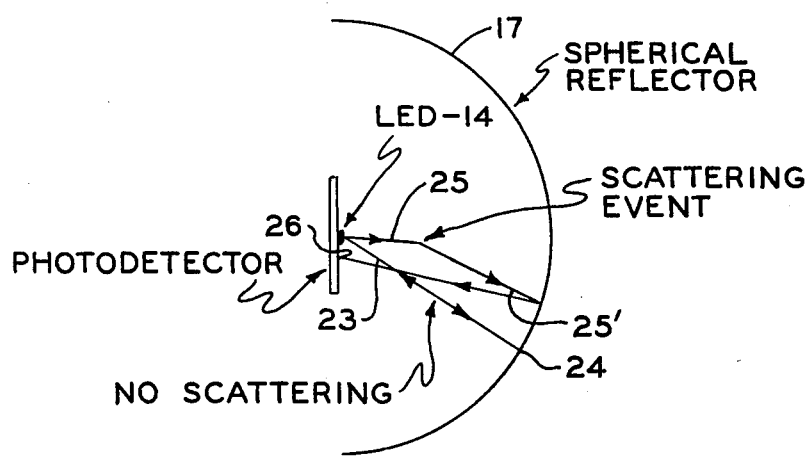
FIGS. 2 and 4 are schematic sketches of the operation of the smoke detector.

The schematic drawing of FIG. 2 shows a beam of light 23 from the LED source 14 being transmitted out to the reflector 17 at point 24 and being reflected along the same path bath to the LED. This beam is not scattered. The next beam of light 25 in FIG. 2 has a scattering event due to smoke particles and the scattered beam 25', when reflected by mirror 17, returns to the photodetector at point 26 to provide a signal. As described above, typical photoelectric smoke detector configurations collect only a small fraction of the smoke-scattered light. This apparatus, by means of the spherical reflector collects all of the light scattered through small angles in both the forward and backward scatter directions.

Figure 4:
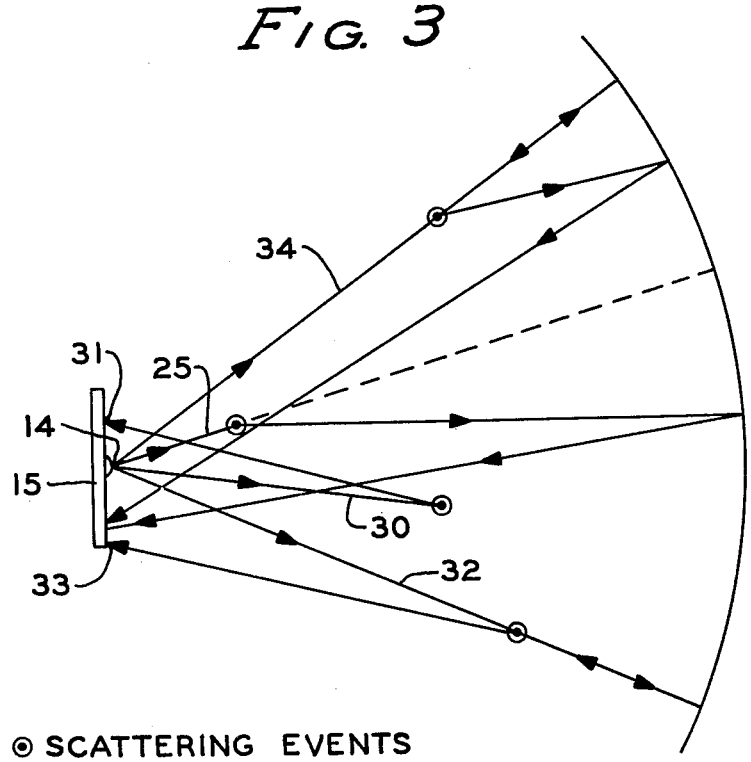

FIG. 4 (similar to FIG. 2 but in more detail) shows an example of forward and of backward scatter of a transmitted beam and of forward and backward scatter of a reflected beam. Thus, curve 25 is an example of forward scatter of a transmitted beam which is described with respect to FIG. 2. Curve 30 is an example of backward scatter of a transmitted beam impinging on the detector at point 31. Curve 32 is an example of forward scatter of a reflected beam which impinges on the detector at 33, and curve 34 is an example of backward scatter of a reflected beam.

The embodiments of the invention in which an exclusive property or right is claimed are defined as follows:

1. Optical smoke detector apparatus comprising:
   a smoke sensing chamber having air inlet and outlet means;
   a light emitter;
   an optical sensor in said chamber having a face comprising a light receiver, said light emitter being mounted on said sensor, said light receiver being of a relatively large area with respect to said light emitter;
   spherical light reflector means mounted in said chamber such that the light emitter is located at the center of curvature of the spherical light reflector means;
   the light being directed from said light emitter onto said light reflecting means and not onto said light receiver, whereby the light directed on said spherical light reflecting means is reflected back to said light emitter without falling on said light receiver; and whereby in the presence of smoke in said chamber, light is scattered thereby, and falls on said light receiving portion to indicate the presence of said smoke.

2. The apparatus in accordance with claim 1 wherein said light receiving portion is substantially planar, with said light emitting portion comprising an LED (light emitting diode) mounted in the middle of said light receiving portion, the LED constructed to emit light into a forward direction and does not direct illumination back onto the light receiving portion.

3. The apparatus in accordance with claim 1 wherein said light emitting portion is an infrared source and said optical sensor light receiving portion is sensitive to the infrared.

4. An improved smoke sensing chamber for an optical smoke detector apparatus comprising:
a smoke sensing chamber;
spherical mirror means in said chamber;
light source means mounted at the center of curvature of said mirror means in said chamber;
light detector means surrounding said light source means in said chamber;
the light from said source being forward directed onto said spherical mirror means and not onto said surrounding light detector means, whereby the light directed on said mirror means is reflected back to said source without falling on said light detector means;
and whereby in the presence of smoke in said chamber the light and the reflected light is scattered by the smoke particles and the scattered light falls on the light detector means to indicate the presence of said smoke.

5. The apparatus in accordance with claim 4 wherein said light source means is an infrared source.

6. The apparatus in accordance with claim 5 wherein said infrared source is a gallium arsenide light emitting diode (LED).

7. The apparatus in accordance with claim 5 wherein said light detector means is sensitive to the infrared source.

* * * * *